(12) United States Patent
Jensen, II

(10) Patent No.: US 11,944,528 B2
(45) Date of Patent: Apr. 2, 2024

(54) MALE INCONTINENCE SLEEVE

(71) Applicant: Jonathan K. Jensen, II, Cambridge, MA (US)

(72) Inventor: Jonathan K. Jensen, II, Cambridge, MA (US)

(*) Notice: Subject to any disclaimer, the term of this patent is extended or adjusted under 35 U.S.C. 154(b) by 743 days.

(21) Appl. No.: 17/125,282

(22) Filed: Dec. 17, 2020

(65) Prior Publication Data

US 2021/0378809 A1 Dec. 9, 2021

Related U.S. Application Data

(60) Provisional application No. 63/036,813, filed on Jun. 9, 2020.

(51) Int. Cl.
*A61F 2/00* (2006.01)

(52) U.S. Cl.
CPC .......... *A61F 2/0054* (2013.01); *A61F 2/0004* (2013.01); *A61F 2/0009* (2013.01); *A61F 2/0031* (2013.01)

(58) Field of Classification Search
CPC .... A61F 2/0004; A61F 2/0009; A61F 2/0031; A61F 2/0054; A61F 6/02; A61F 6/04; A61F 2006/045; A61F 2006/046; A61F 2006/047
See application file for complete search history.

(56) References Cited

U.S. PATENT DOCUMENTS

| | | | |
|---|---|---|---|
| 5,630,429 A * | 5/1997 | Dann | A61F 5/48 128/885 |
| 5,746,222 A | 5/1998 | Simon et al. | |
| 6,461,340 B1 | 10/2002 | Lenker | |
| 7,926,489 B2 * | 4/2011 | Anderson | A61F 13/471 128/885 |
| 2020/0297470 A1 * | 9/2020 | Glisan | A61F 2/0031 |

* cited by examiner

*Primary Examiner* — Keri J Nelson
(74) *Attorney, Agent, or Firm* — Kunzler Bean & Adamson (57) ABSTRACT

Disclosed herein is a sleeve for reducing involuntary leakage of a flowable material from a urethral meatus of a penis. The sleeve comprises a body that is configured to temporarily receivably retain a glans penis. When the glans penis is temporarily receivably retained by the body, the body applies an inwardly-directed pressure to the glans penis to close a urethral meatus of the glans penis.

20 Claims, 11 Drawing Sheets

MALE INCONTINENCE SLEEVE

CROSS-REFERENCE TO RELATED APPLICATION

This application claims the benefit of U.S. Provisional Patent Application No. 63/036,813 filed Jun. 9, 2020, which is incorporated herein by reference.

FIELD

The present disclosure relates generally to male incontinence, and more particularly to devices and methods for reducing involuntary fluid leakage associated with male incontinence.

BACKGROUND

Involuntary urine leakage due to male incontinence is a common problem. According to some known techniques, urine leakage from the urethra is reduced by clamping or wrapping an external device onto the penis or using a device to constrict or plug the penis. However, conventional external devices are uncomfortable to wear and not particularly equipped to allow for voluntary urination while worn. Moreover, many external devices restrict blood flow to the penis when worn. Some conventional external devices are awkward and cumbersome when worn in conjunction with certain apparel, such as athletic apparel, or when used in conjunction with certain activities.

In addition to problems associated with male urinary incontinence, often ointments, medications, or other flowable materials, placed in the urethra during certain procedures, can leak from the urethra, which as defined herein, can be considered a form of male incontinence because the patient does not have voluntary control over the leakage of the flowable material. Sometimes, external devices, such as clamps, are used to prevent leakage of flowable material from the urethra. However, these external devices suffer from the same above-referenced shortcomings associated with external devices for treating male incontinence.

SUMMARY

The subject matter of the present application has been developed in response to the present state of the art, and in particular, in response to the problems and needs of conventional devices and methods for addressing male incontinence, that have not yet been fully solved. In view of the foregoing, the subject matter of the present application has been developed to provide apparatuses and methods for reducing involuntary leakage of urine, commonly associated with male urinary incontinence, or leakage of other flowable materials, that overcome many of the above-discussed shortcomings of the prior art. According to some examples, disclosed herein is a sleeve that is easy to put on, has an insubstantial size and streamlined shape, provides simple and quick access for voluntary urination, does not compromise blood flow to the penis to the extent associated with prior art devices, and helps to reduce involuntary leakage of urine or other flowable material without excessive pressure on the penis.

Disclosed herein is a sleeve for reducing involuntary leakage of flowable material from a urethral meatus of a penis. The sleeve comprises a body that is configured to temporarily receivably retain a glans penis. When the glans penis is temporarily receivably retained by the body, the body applies an inwardly-directed pressure to the glans penis to close a urethral meatus of the glans penis. The preceding subject matter of this paragraph characterizes example 1 of the present disclosure.

The body comprises a cylindrical section, a conical section, and a receptacle defined by the cylindrical section and the conical section. The body is configured to temporarily receivably retain the glans penis within the receptacle. The preceding subject matter of this paragraph characterizes example 2 of the present disclosure, wherein example 2 also includes the subject matter according to example 1, above.

The receptacle comprises a proximal opening defined by the cylindrical section and a distal opening defined by the conical section. The proximal opening is larger than the distal opening. The preceding subject matter of this paragraph characterizes example 3 of the present disclosure, wherein example 3 also includes the subject matter according to example 2, above.

The proximal opening has a circular shape. The distal opening has a non-circular shape. The preceding subject matter of this paragraph characterizes example 4 of the present disclosure, wherein example 4 also includes the subject matter according to example 3, above.

The non-circular shape of the distal opening is one of an elliptical shape, an elongated shape, an ovular shape, or a racetrack shape. The preceding subject matter of this paragraph characterizes example 5 of the present disclosure, wherein example 5 also includes the subject matter according to example 4, above.

The body further comprises perforations located along the body between the proximal opening and the distal opening. The preceding subject matter of this paragraph characterizes example 6 of the present disclosure, wherein example 6 also includes the subject matter according to any one of examples 3-5, above.

The sleeve further comprising pads. Each one of the pads is coupled to an interior surface of the conical section of the body on opposite sides of the distal opening. The pads define a converging portion of the receptacle. The preceding subject matter of this paragraph characterizes example 7 of the present disclosure, wherein example 7 also includes the subject matter according to any one of examples 3-6, above.

Each one of the pads comprises an engagement surface, configured to engage the glans penis. The engagement surface of each one of the pads is at least one of convex or concave. The preceding subject matter of this paragraph characterizes example 8 of the present disclosure, wherein example 8 also includes the subject matter according to example 7, above.

Each one of the pads defines a corresponding one of two opposing linear sides of the distal opening of the receptacle. The preceding subject matter of this paragraph characterizes example 9 of the present disclosure, wherein example 9 also includes the subject matter according to example 8, above.

The receptacle has a width, extending from a left side of the body to a right side of the body, and a length, extending from a back side of the body to a front side of the body. The width of the receptacle, along the conical section of the body, is defined by the pads. A rate of convergence of the width of the receptacle, along the conical section of the body, is higher than a rate of convergence of the length of the receptacle, along the conical section of the body. The preceding subject matter of this paragraph characterizes example 10 of the present disclosure, wherein example 10 also includes the subject matter according to any one of examples 7-9, above.

The sleeve further comprises tabs each coupled to and extending laterally away from an exterior surface of the conical section of the body at a corresponding one of the left side and the right side of the body. The preceding subject matter of this paragraph characterizes example 11 of the present disclosure, wherein example 11 also includes the subject matter according to example 10, above.

Each one of the tabs comprises an exterior surface and a rib that protrudes from the exterior surface. The preceding subject matter of this paragraph characterizes example 12 of the present disclosure, wherein example 12 also includes the subject matter according to example 11, above.

The tabs are pullable away from each other to increase the width of the receptacle at the distal opening. The preceding subject matter of this paragraph characterizes example 13 of the present disclosure, wherein example 13 also includes the subject matter according to any one of examples 11-12, above.

The width of the receptacle at the distal opening is less than the length of the receptacle at the distal opening. The preceding subject matter of this paragraph characterizes example 14 of the present disclosure, wherein example 14 also includes the subject matter according to any one of examples 10-13, above.

The sleeve further comprises a ring coupled to the conical section of the body. The ring defines the distal opening. The body is made of a first resiliently flexible material. The ring is made of a second resiliently flexible material. A stiffness of the first resiliently flexible material is less than a stiffness of the second resiliently flexible material. The preceding subject matter of this paragraph characterizes example 16 of the present disclosure, wherein example 15 also includes the subject matter according to any one of examples 3-14, above.

The body is made of an elastic material. The preceding subject matter of this paragraph characterizes example 16 of the present disclosure, wherein example 15 also includes the subject matter according to any one of examples 1-15, above.

The body comprises a flap portion and a receptacle portion. The flap portion and the receptacle portion are coupled together at a fold line that divides the body into the flap portion and the receptacle portion. The flap portion and the receptacle portion taper to the fold line. A central channel extends along an entirety of the body. A portion of the central channel defined by the receptacle portion is shaped to receive a tip portion of the glans penis. A length of the flap portion is greater than a length of the receptacle portion such that when the body is folded at the fold line, the flap portion overlaps an entirety of the receptacle portion. The preceding subject matter of this paragraph characterizes example 17 of the present disclosure, wherein example 17 also includes the subject matter according to any one of examples 1-16, above.

A shape of the central channel at the flap portion is non-circular. The preceding subject matter of this paragraph characterizes example 18 of the present disclosure, wherein example 18 also includes the subject matter according to example 17, above.

The body comprises a flap portion and a pair of receptacle tabs. The receptacle tabs of the pair of receptacle tabs are opposite and spaced apart from each other. The flap portion and the pair of receptacle tabs are coupled together at a fold line that divides the body into the flap portion and the pair of receptacle tabs. The flap portion and the pair of receptacle tabs taper to the fold line. A central channel extends along the flap portion of the body. A space between the receptacle tabs is shaped to receive a tip portion of the glans penis. A length of the flap portion is greater than a length of each receptacle tab of the pair of receptacle tabs such that when the body is folded at the fold line, the flap portion overlaps an entirety of the pair of receptacle tabs. The preceding subject matter of this paragraph characterizes example 19 of the present disclosure, wherein example 19 also includes the subject matter according to any one of examples 1-18, above.

Further disclosed herein is a method of regulating leakage of a flowable material from a urethral meatus of a penis. The method comprises temporarily receivably retaining a glans penis of a penis within a receptacle defined by a body of a sleeve with the sleeve in tension. The method also comprises compressing a urethral meatus of the glans penis, due to tension in the sleeve, to close the urethral meatus. The method further comprises manually selectively releasing tension in the sleeve to decompress the urethral meatus and open the urethral meatus. The preceding subject matter of this paragraph characterizes example 20 of the present disclosure.

The described features, structures, advantages, and/or characteristics of the subject matter of the present disclosure may be combined in any suitable manner in one or more examples and/or implementations. In the following description, numerous specific details are provided to impart a thorough understanding of examples of the subject matter of the present disclosure. One skilled in the relevant art will recognize that the subject matter of the present disclosure may be practiced without one or more of the specific features, details, components, materials, and/or methods of a particular example or implementation. In other instances, additional features and advantages may be recognized in certain examples and/or implementations that may not be present in all examples or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended numbered paragraphs, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific examples that are illustrated in the appended drawings. Understanding that these drawings, which are not necessarily drawn to scale, depict only certain examples of the subject matter and are not therefore to be considered to be limiting of its scope, the subject matter will be described and explained with additional specificity and detail through the use of the drawings, in which.

DETAILED DESCRIPTION

Reference throughout this specification to "one example," "an example," or similar language means that a particular feature, structure, or characteristic described in connection with the example is included in at least one example of the present disclosure. Appearances of the phrases "in one example," "in an example," and similar language throughout this specification may, but do not necessarily, all refer to the same example. Similarly, the use of the term "implementation" means an implementation having a particular feature, structure, or characteristic described in connection with one or more examples of the present disclosure, however, absent an express correlation to indicate otherwise, an implementation may be associated with one or more examples.

Figure 1:
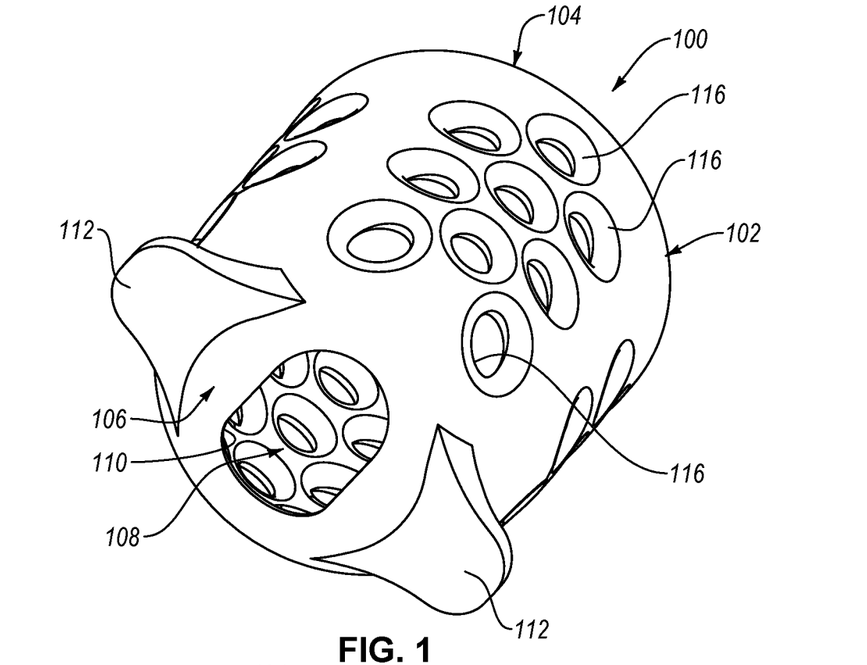
FIG. 1 is a schematic, perspective view of a sleeve for reducing involuntary leakage of urine or other flowable material, according to one or more examples of the present disclosure.
Figure 2:
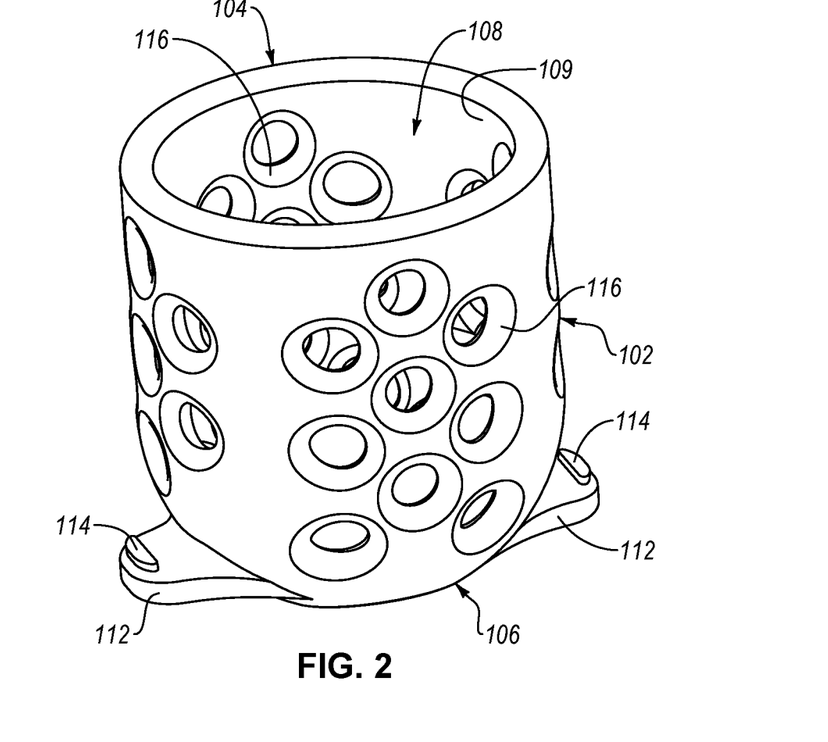
FIG. 2 is a schematic, perspective view of the sleeve of FIG. 1, according to one or more examples of the present disclosure.

Referring to FIGS. 1 and 2, and according to some examples, disclosed herein is a sleeve 100 or sheath for reducing involuntary leakage of fluid associated with male incontinence, such as involuntary urine leakage associated with male urinary incontinence or involuntary leakage of other flowable materials. The following proceeds with reference to sleeves for reducing involuntary urine leakage associated with male urinary incontinence. However, it is recognized that the sleeves also help to reduce the involuntary leakage of any flowable material from the urethra, which as mentioned above is a form of male incontinence. Accordingly, any reference to male urinary incontinence or urine leakage from the urethra can be interchangeable with male fluid incontinence or any leakage of a flowable material from the urethra.

The sleeve 100 includes a body 102 that extends from a proximal end 104 of the body 102 to a distal end 106 of the body 102. The distal end 106 is opposite the proximal end 104. The body 102 has a cylindrical section 144 that defines the proximal end 104 and a conical section 146 that defines the distal end 106 (see, e.g., FIG. 3). In certain examples, the cylindrical section 144 has a substantially constant outer diameter. In contrast, in certain examples, an outer diameter of the conical section 146 continually decreases in a direction away from the cylindrical section 144. In this manner, the body 102 mimics the shape of the glans penis 132 of the penis 130 (see, e.g., FIG. 7). Accordingly, as defined herein, in some examples, the conical section is conical in that it has a generally conical shape, or is circumferentially closed and has a major dimension (e.g., diameter) that decreases along a length of the conical section. Because the body 102 is relatively thin, the body 102, thus generally matching the shape of the glans penis 132, promotes non-intrusiveness and discreetness of the sleeve 100 when worn.

Figure 9:
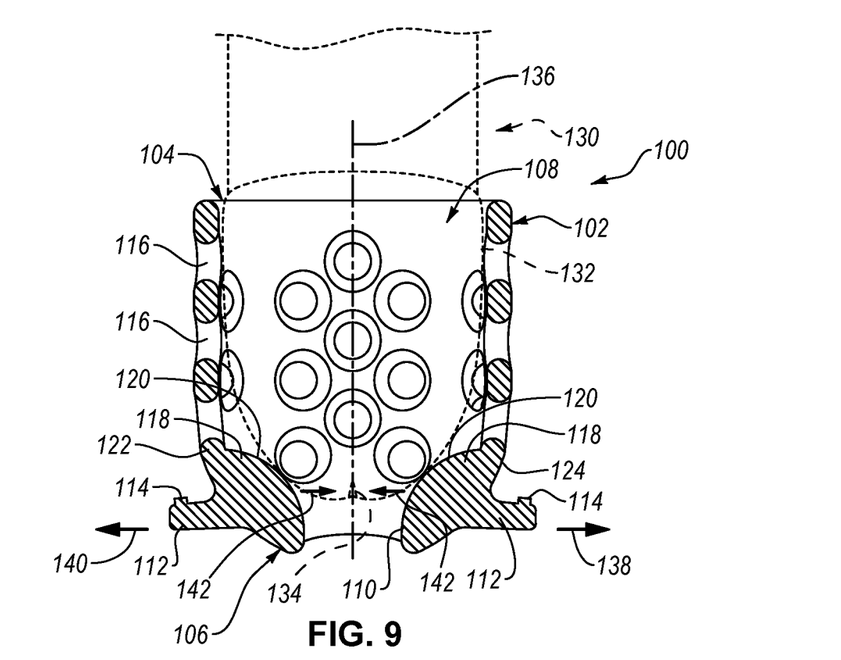
FIG. 9 is a schematic, cross-sectional, top plan view of the sleeve of FIG. 1, taken along the line 6-6 of FIG. 5, and shown with a penis received in the sleeve, according to one or more examples of the present disclosure.

The body 102 defines a receptacle 108 that extends from the proximal end 104 to the distal end 106. In some examples, the body 102 has a substantially constant thickness. Accordingly, the receptacle 108 shares the same general shape as the body 102 and, like the body 102, mimics the shape of the glans penis 132. For example, an inner dimension of the conical section 146 continually decreases in a direction away from the cylindrical section 144. In this manner, the receptacle 108 is conducive to receiving and retaining the glans penis 132 as schematically shown in FIG. 9. The receptacle 108 includes a proximal opening 109 at the proximal end 104 of the body 102 (e.g., defined by the cylindrical section 144) and a distal opening 110 at the distal end 106 of the body 102 (e.g., defined by the conical section 146). Therefore, the receptacle 108 includes and extends from the proximal opening 109 to the distal opening 110. The proximal opening 109 is larger than the distal opening 110. In one example, the proximal opening 109 has a circular shape and the distal opening 110 has a non-circular shape, such as an elliptical, an elongated, an ovular, or a racetrack shape.

In some examples, the body 102 further includes perforations 116 formed in one or both of the cylindrical section 144 or the conical section 146. The perforations 116 are formed in the wall defining the body 102 and are located along the body 102 between the distal opening 110 and the proximal opening 109. Each one of the perforations 116 is a through-opening or through-aperture that extends entirely through a thickness of the body 102. Accordingly, the receptacle 108 is open to an exterior of the sleeve 100 via the perforations 116. In the illustrated example, each one of the perforations 116 has a circular shape. However, the perforations 116 can have shapes other than circular. Moreover, the perforations 116 can be grouped together according to any of various patterns. The perforations 116 help to promote or reduce restriction of blood flow to the penis 130 when the sleeve 100 is worn. Additionally, the perforations 116 may help with the breathability of the sleeve 100 and/or reducing perspiration.

Figure 4:
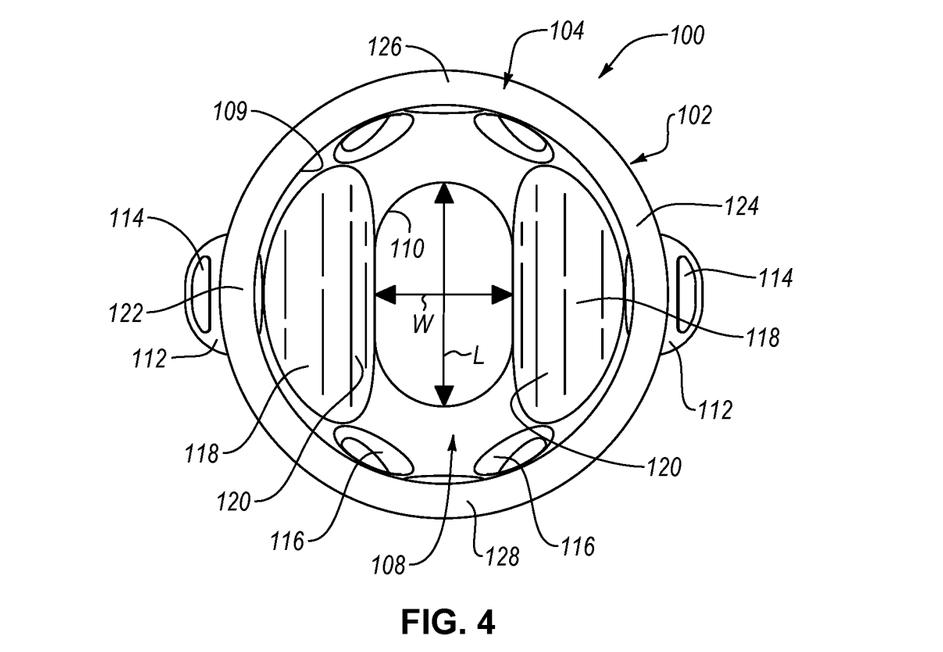
FIG. 4 is a schematic, back view of the sleeve of FIG. 1, according to one or more examples of the present disclosure.
Figure 7:
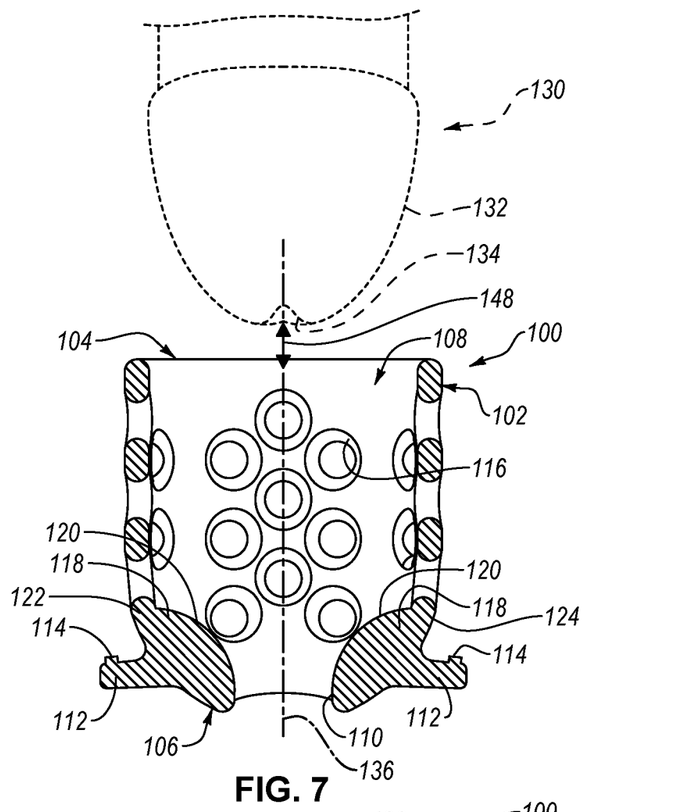
FIG. 7 is a schematic, cross-sectional, top plan view of the sleeve of FIG. 1, taken along the line 6-6 of FIG. 5, and shown with a penis in position for reception in the sleeve, according to one or more examples of the present disclosure.
Figure 8:
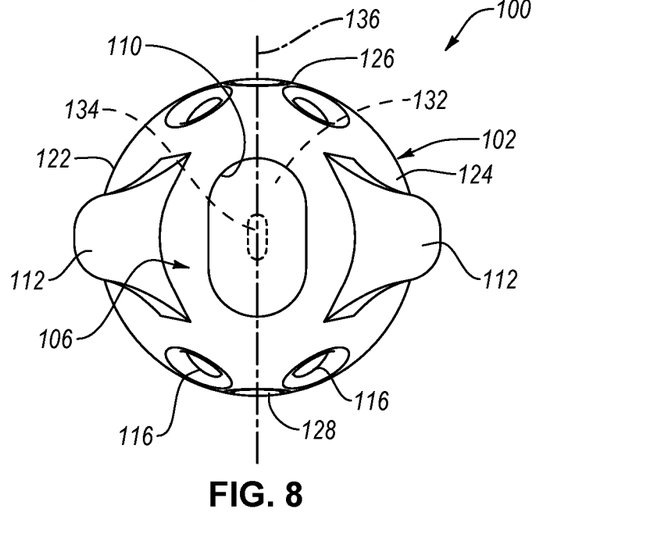
FIG. 8 is a schematic, front view of the sleeve of FIG. 1, shown with a penis in position for reception in the sleeve, according to one or more examples of the present disclosure.

Referring to FIG. 4, the body 102 includes a left side 122 and a right side 124. The left side 122 is opposite the right side 124. The body 102 also includes a back side 126 and a front side 128. The back side 126 is opposite the front side 128. It is recognized that, depending on the orientation of the sleeve 100, the right side 124 and the left side 122 are reversible and the back side 126 and the front side 128 are reversible. However, as will be described, when worn on the penis 130, the right side 124 corresponds with the right side of the wearer, the left side 126 corresponds with the left side of the wearer, the back side 126 corresponds with the back of the wearer and the front side 128 corresponds with the front of the wearer. As shown in FIGS. 7 and 8, the right side of the wearer is separated from the left side of the wearer by a sagittal plane 136 of the wearer. Essentially, the sagittal plane 136 divides the wearer's body and penis into the right side and the left side.

In some examples, the body 102 is made of an elastic material, such as silicone, styrene-ethylene-butylene-styrene (SEBS), and the like. Accordingly, the body 102 is capable of being stretched and resiliently returning to an original shape. In this manner, the body 102 can be stretched around the glans penis 132 to retain the glans penis 132 in the receptacle 108 of the body 102.

Figure 3:
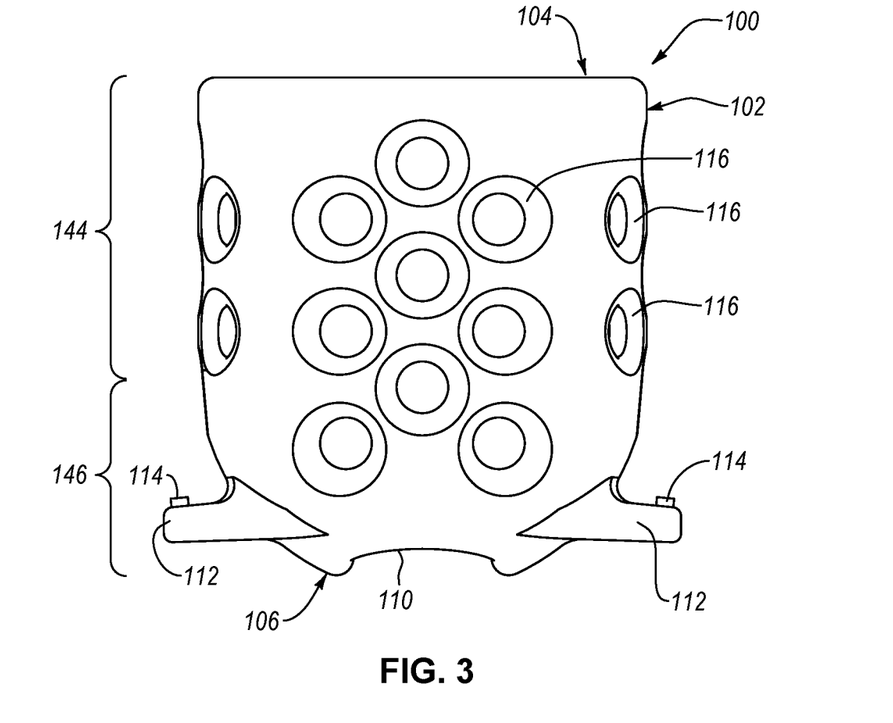
FIG. 3 is a schematic, top plan view of the sleeve of FIG. 1, according to one or more examples of the present disclosure.
Figure 5:
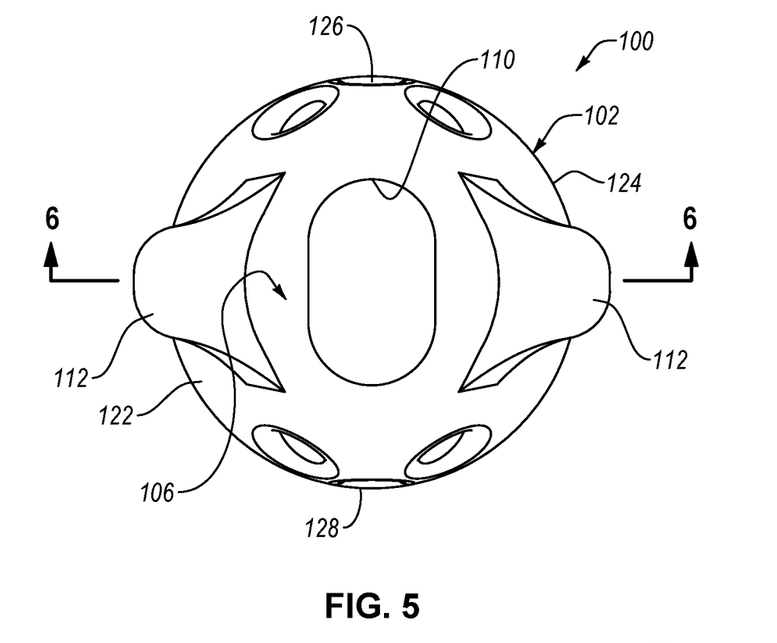
FIG. 5 is a schematic, front view of the sleeve of FIG. 1, according to one or more examples of the present disclosure.

According to certain examples, the sleeve 100 includes a pair of tabs 112 coupled to and extending laterally away from an exterior surface of the conical section 146 of the body 102. As shown in FIGS. 3 and 5, each one of the tabs 112 is coupled to and extends laterally away from a corresponding one of the right side 124 and the left side 122 of the body 102, in directions perpendicular to the sagittal plane 136. Accordingly, the tabs 112 extend from the body 102 in opposite directions relative to each other. However, in some examples, the tabs 112 extend laterally away from a corresponding one of the right side 124 and the left side 122 of the body 102 in directions oblique to the sagittal plane 136 (e.g., forwardly angled toward the distal end 106).

The tabs 112 are coupled to the conical section 146 of the body 102 proximate the distal opening 110. In some examples, the tabs 112 are closer to the distal opening 110 than to the cylindrical section 144 of the body 102. According to some examples, the tabs 112 include ribs 114 that help a wearer grip and pull the tabs 112. Each one of the tabs 112 includes at least one rib 114 that protrudes from an exterior surface of the corresponding tab 112. In the illustrated example, the ribs 114 extend from the exterior surfaces of the tabs 112 toward the cylindrical section 144 of the body 102. However, in other examples, the ribs 114 extend from exterior surface of the tabs 112 away from the cylindrical section 144 of the body 102. The tabs 112, ribs 114, and the body 102 form a one-piece monolithic construction in some examples.

Referring to FIG. 4, according to the illustrated examples, the distal opening 110 has a length L greater than a width W. Accordingly, the distal opening 110 is elongated in the lengthwise direction. The distal opening 110 is oriented relative to the body 102 such that the length L of the distal opening 110 extends from the back side 126 of the body 102 to the front side 128 of the body 102. Accordingly, the length L of the distal opening 110 divides the left side 122 of the body 102 from the right side 124 of the body 102. With the length L oriented in this manner, the width W of the distal opening 110 extends from the left side 122 of the body 102 to the right side 124 of the body 102. Accordingly, the width W of the distal opening 110 divides the back side 126 of the body 102 from the front side 128 of the body 102. When the sleeve 100 is properly worn by the wearer, the length L of the distal opening 110 is parallel to (e.g., co-planar with) the sagittal plane 136 of the wearer and the width W of the distal opening 110 is perpendicular to the sagittal plane 136 of the wearer. Although shown to have a length L greater than a width W, in some examples, the length L is not greater than the width W (e.g., a square or circular shaped distal opening 110).

Figure 6:
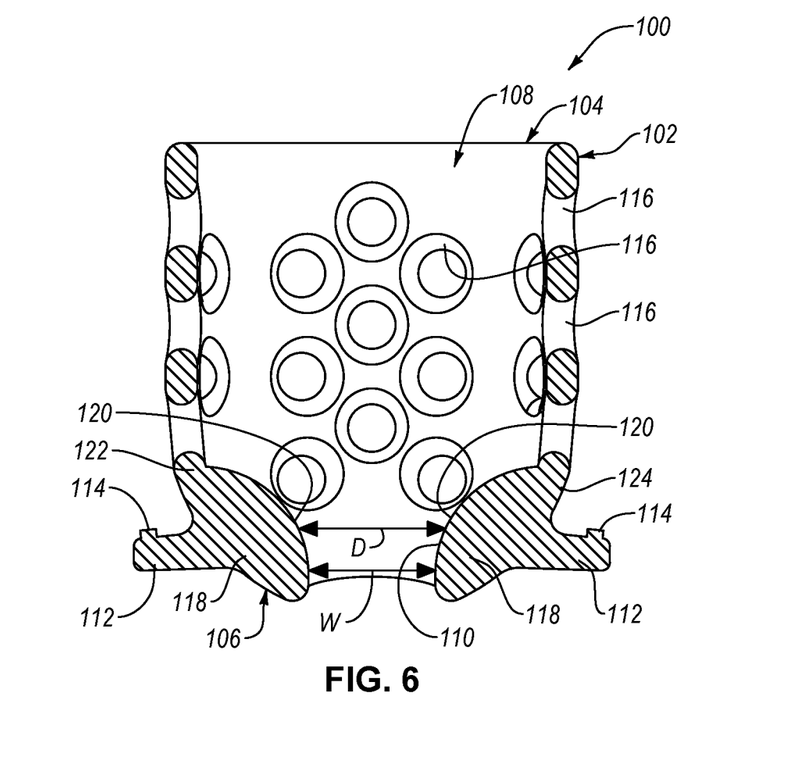
FIG. 6 is a schematic, cross-sectional, top plan view of the sleeve of FIG. 1, taken along the line 6-6 of FIG. 5, according to one or more examples of the present disclosure.

Referring to FIGS. 4 and 6, the sleeve 100 additionally includes a pair of pads 118 coupled to the interior surface of the conical section 146 of the body 102. The pads 118 extend into and partially define the receptacle 108. Accordingly, the pads 118 define a converging portion of the receptacle 108. The pads 118 are located on opposite sides of the distal opening 110 across the width W of the distal opening 110. As shown, no pads are present on opposite sides of the distal opening 110 across the length L of the distal opening 110. Accordingly, each one of the pads 118 is coupled to and extends from a corresponding one of the right side 124 and the left side 122 of the body 102. In some examples, the pads 118 are integrally formed with the body 102 such that the body 102 and the pads 118 form a monolithic, one-piece, and seamless construction.

Moreover, each one of the pads 118 includes an engagement surface 120 that is configured to engage the glans penis 132 when the sleeve 100 is worn. A portion of the engagement surface 120 of each one of the pads 118 at least partially defines a corresponding right side and left side of the distal opening 110. In the illustrated example, the right side and the left side of the distal opening 110 are generally linear and a back side and a front side of the distal opening 110 are generally curved. Therefore, the portions of the engagement surfaces 120 of the pads 118 defining the distal opening 110 are generally linear in back view (see, e.g., FIG. 4). However, in top plan view (see, e.g., FIG. 6), the engagement surfaces 120 are contoured (e.g., convex) such that a distance D between the engagement surfaces 120 decreases at a first rate (e.g., a first rate of convergence) in a direction from the proximal end 104 to the distal end 106.

Figure 16:
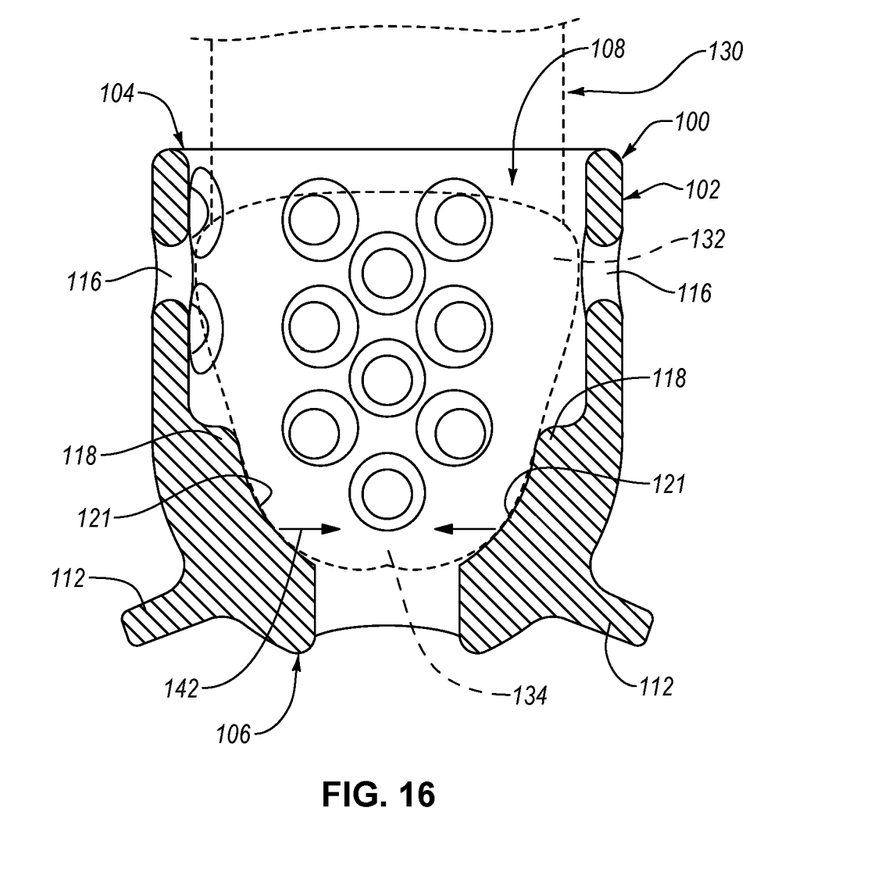
FIG. 16 is a schematic, cross-sectional, top plan view of a sleeve for reducing involuntary leakage of urine or other flowable material, taken along a line similar to the line 6-6 of FIG. 5, and shown with a penis received in the sleeve, according to one or more examples of the present disclosure.

However, it is recognized that the first rate need not be constant. For example, the engagement surfaces 120 may include convex and concave portions and have one or more inflection points. For example, as shown in FIG. 16, the pads 118 of the sleeve 100 can include engagement surfaces 121 that are concave along at least a portion of the engagement surfaces 121. While the distance between the concave engagement surfaces 121 decreases in the direction from the proximal end 104 to the distal end 106, the rate at which the distance decreases is initially less than that of the convex engagement surfaces 120 of the sleeve 100 of FIGS. 1-11. Accordingly, while providing the same functionality as the convex engagement surfaces 120, the concavity of the engagement surfaces 121 may be more comfortable to some users than others.

The distance D between the engagement surface 120 is equal to the width W of the distal opening 110 at the proximal end 104. The first rate is higher than a second rate of the decrease of the inner dimension of the conical section 146 between the back side 126 and the front side 128 of the body 102 (e.g., a second rate of convergence). Accordingly, the receptacle 108 is thinner between the pads 118 than between the back side 126 and the front side 128. In some examples, the tabs 112 and the pads 118 are made of the same material as the body 102. Additionally, in certain examples, the pads 118 and the body 102 form a one-piece monolithic construction.

Referring to FIGS. 7 and 8, according to one example, a method of using the sleeve 100 to help reduce involuntary urine leakage includes orienting the sleeve 100 into a receiving orientation relative to the glans penis 132 of the wearer. In the receiving orientation, the left side 122 of the body 102 is aligned with the left side of the wearer, the right side 124 of the body 102 is aligned with the right side of the wearer, the back side 126 of the body 102 is aligned with the back of the wearer, and the front side 128 of the body 102 is aligned with the front of the wearer. In other words, in the receiving orientation, the width W of the distal opening 110 is perpendicular to the sagittal plane 136 of the wearer and the length L of the distal opening 110 is parallel to the sagittal plane 136. The urethra of the wearer extends along the penis 130, through the glans penis 132, and opens to the outside of the body at a urethral meatus 134. When open, the urethral meatus 134, or external urethral orifice, has a generally elongated shape and is oriented such that the sagittal plane 136 is parallel to the length of the urethral meatus 134 (see, e.g., FIG. 8). With the sleeve 100 in the receiving orientation, the width W of the distal opening 110 is parallel to a width of the urethral meatus 134 and the length L of the distal opening 110 is parallel to the length of the urethral meatus 134. As shown in FIG. 7, with the sleeve 100 in the receiving orientation, the sleeve 100 is moved relative to the glans penis 132, as indicted by directional arrows 148, to insert the glans penis 132 into the receptacle 108 or receive the glans penis 132 in the receptacle 108.

Figure 10:
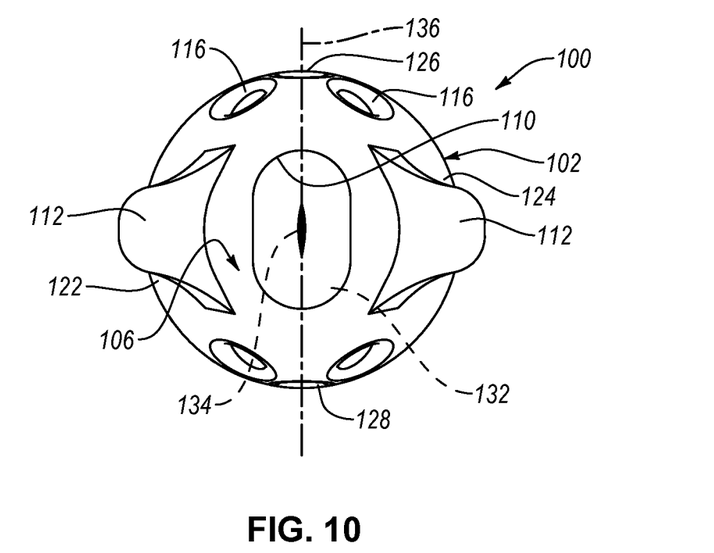
FIG. 10 is a schematic, front view of the sleeve of FIG. 1, shown with a penis received in the sleeve, according to one or more examples of the present disclosure.

Referring to FIGS. 9 and 10, as the glans penis 132 is inserted along the receptacle 108, the tip of the glans penis 132 engages the engagement surfaces 120 of the pads 118. Due to the constriction of the receptacle 108 by the pads 118 along the width W of the distal opening 110, but not along the length L of the distal opening 110, engagement between the glans penis 132 and the engagement surfaces 120 of the pads 118 generates opposing inwardly-directed forces 142 (e.g., compressive forces (e.g., pinching)), due to the sleeve 100 being stretched and in tension when positioned about the glans penis 132, parallel to the width W of the distal opening 110, on the tip of the glans penis 132. The inwardly-directed forces 142 act to close the urethral meatus 134, across the width of the urethral meatus 134, as shown in FIGS. 9 and 10. Because the urethral meatus 134 is closed, involuntary urinary excretion through the urethral meatus 134 is prevented.

Other portions of the body 102 apply a slight compressive force on the glans penis 132, due to the tension in the body 102, to retain the glans penis 132 in the receptacle and to keep the urethral meatus 134 closed. While the compressive force on the glans penis 132 applied by other portions of the body 102 may be sufficient to close the urethral meatus 134, in some examples, forces sufficient to close the urethral meatus 134 are only applied along a single plane and only generated by engagement with the pads 118. In certain examples, the sleeve 100 could be oriented such that the width W of the distal opening 110 is parallel to sagittal plane 136 and the pads 118 close the urethral meatus 134 across the length of the urethral meatus 134. But, the inwardly-directed forces 142 necessary to close the urethral meatus 134 across its length is more than across its width and doing so may result in additional pressure on the wearer.

Figure 11:
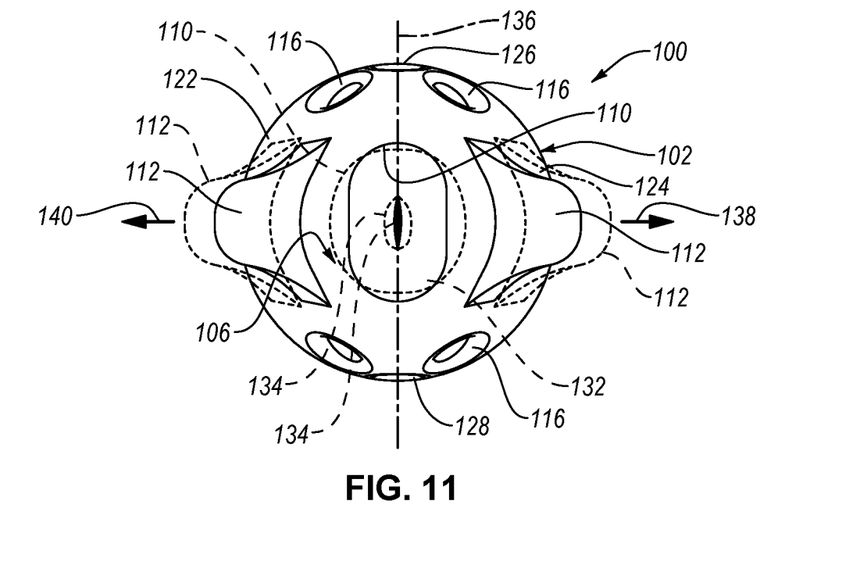
FIG. 11 is a schematic, front view of the sleeve of FIG. 1, showing the sleeve in a compression and a non-compression state, according to one or more examples of the present disclosure.

While wearing the sleeve 100, should the wearer desire to voluntarily urinate, the wearer does not need to remove the sleeve 100. Rather, the tabs 112 of the sleeve 100 facilitate opening of the urethral meatus 134 to allow for voluntary urination. Referring to FIG. 11, with the sleeve 100 retained on the glans penis 132, the wearer may grasp the tabs 112, such as by pinching each one of the tabs 112 with the thumb and forefinger of a corresponding one of the hands of the wearer, and pull the tabs 112 laterally outwardly in opposing directions 138, 140. By pulling the tabs 112, the pads 118 are moved away from each other, thus manually selectively releasing tension in the sleeve 100, and the distal opening 110 is widened, which reduces (e.g., removes) the inwardly-directed forces 142 acting on the glans penis 132 (i.e., takes the sleeve 100 out of tension). The reduction in the inwardly-directed forces 142 allows the urethral meatus 134 to open to facilitate the voluntary discharge of urine from the urethral meatus 134. After voluntary urination is complete, the wearer can release the tabs 112, which brings the pads 118 back together and reintroduces the initial inwardly-directed forces 142 (e.g., due to the reintroduction of tension in the sleeve 100) on the glans penis 132 to again close the urethral meatus 134. In this manner, the wearer can voluntarily urinate without having to remove the sleeve 100.

Figure 17:
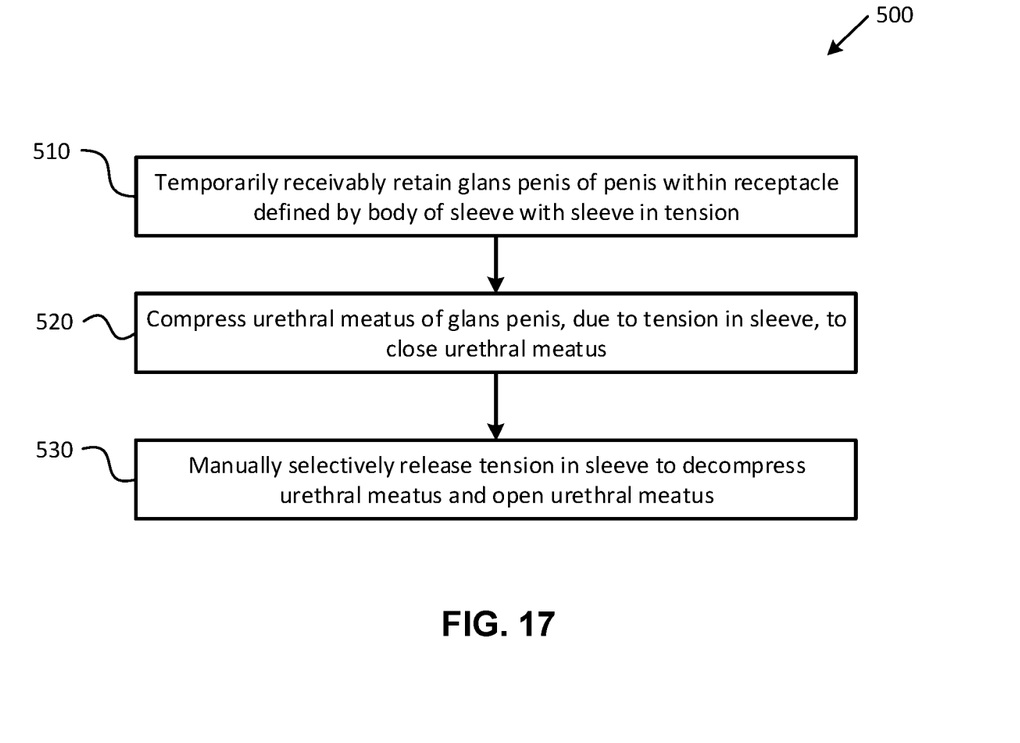
FIG. 17 is a flow chart diagram of a method of regulating leakage of urine or other flowable material from a urethral meatus of a glans penis.

According to another example, as shown in FIG. 17, a method 500 of regulating leakage of flowable material (e.g., urine) from the urethral meatus 134 of the glans penis 132 is shown. The method 500 includes (block 510) temporarily receivably retaining the glans penis 132 of the penis 130 within the receptacle 108 defined by the body 102 of the sleeve 100 with the sleeve 100 in tension. The method 500 additionally includes (block 520) compressing the urethral meatus 134 of the glans penis 132, due to tension in the sleeve 100, to close the urethral meatus 134. The method 500 also includes (block 530) manually selectively releasing tension in the sleeve 100 to decompress the urethral meatus 134 and open the urethral meatus 134.

Figure 14:
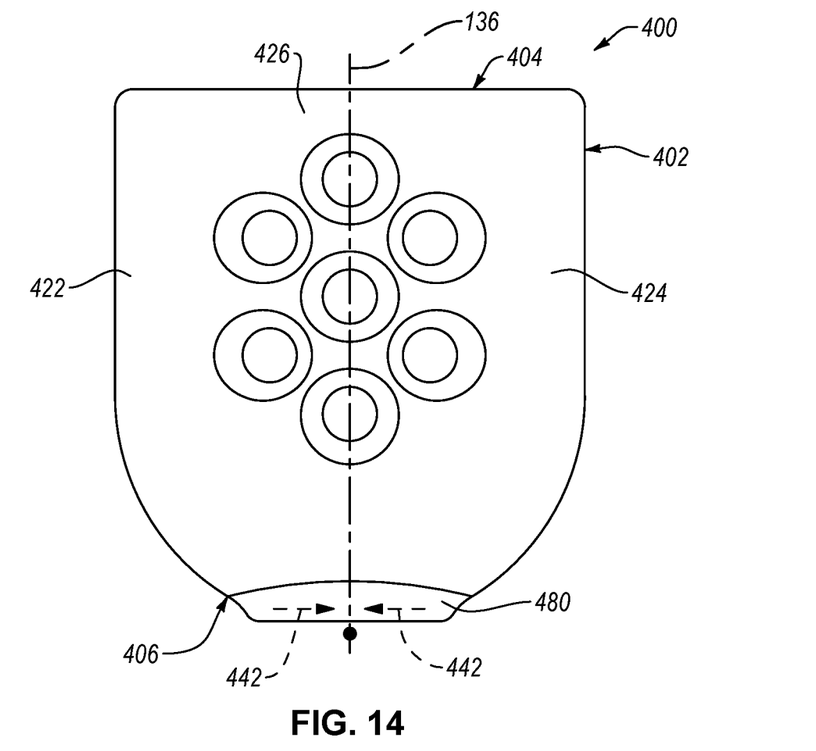
FIG. 14 is a schematic, top plan view of another sleeve, according to one or more examples of the present disclosure.
Figure 15:
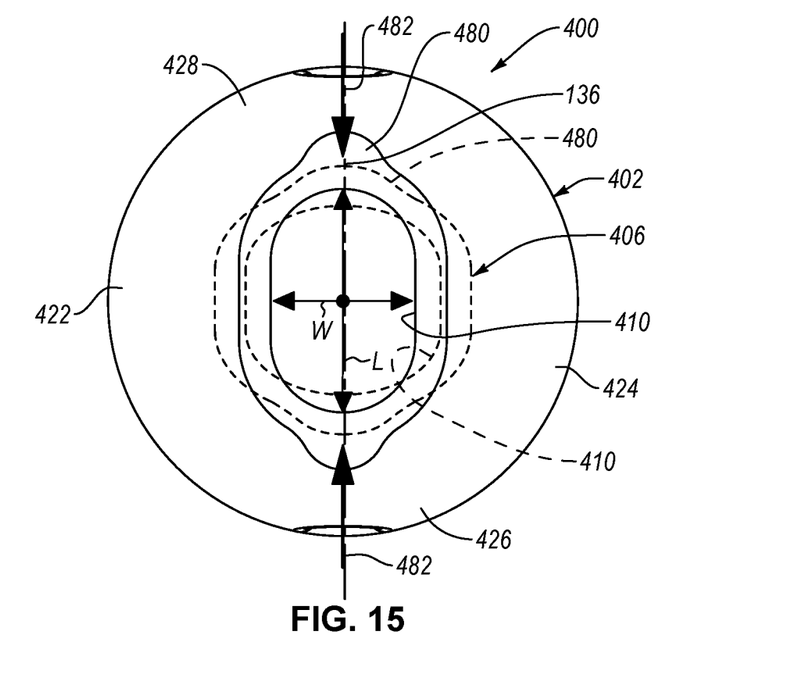
FIG. 15 is a schematic, front view of the sleeve of FIG. 14, according to one or more examples of the present disclosure.

In some examples, the sleeve 100 does not include tabs 112. Referring to FIGS. 14 and 15, one example of a sleeve 400 for reducing involuntary urine leakage associated with male urinary incontinence is shown. The sleeve 400 is similar to the sleeve 100 except the sleeve 400 does not include the tabs 112. Instead, the sleeve 400 includes a ring 480 coupled to a body 402 of the sleeve 400 at a distal end 406 of the body 402, which is opposite a proximal end 404 of the body 402. The ring 480 has an annular shape in certain examples and defines at least a portion of a distal opening 410 of the sleeve 400. Accordingly, the ring 480 can have the same general shape as the distal opening 410. In the illustrated example, the ring 480 and the distal opening 410 are elongated along the sagittal plane 136, when worn, similar to the distal opening 110 of the sleeve 100. Moreover, the sleeve 400 includes pads (not shown), similar to the pads 118 of the sleeve 100, which apply opposing inwardly-directed forces 442 perpendicular to the sagittal plane 136 (e.g. inwardly from a left side 422 and a right side 424 of the body 402), when worn, on the tip of the glans penis 132 to close the urethral meatus 134.

Like the body 402, the ring 480 is made of a resiliently flexible material. The stiffness of the material of the ring 480 may be greater than that of the body 402. In some examples, the ring 480 is made of a polymeric material, such as a urethane (e.g., a thermoplastic polyurethane), or other resiliently flexible material. When the wearer desires to voluntarily urinate, the wearer can compress the ring 480 from a back side 426 and a front side 428 of the body 402 to apply opposing compressive forces 482 on the ring 480. The compressive forces 482 cause the ring 480 to deform as shown in dashed line in FIG. 15, such that the ring 480, and thus the distal opening 410, shortens and widens (e.g., the length L decreases and the width W increases). The widening of the distal opening 410 reduces or eliminates the opposing inwardly-directed forces 442 acting on the glans penis 132, which allows the urethral meatus 134 to open to facilitate the voluntary discharge of urine from the urethral meatus 134. When the compressive forces 482 are released from the ring 480, the ring 480 returns to its original shape and the inwardly-directed forces 442 are again applied to the glans penis 132 to re-close the urethral meatus 134. In some examples, the ring 480 can be compressed (e.g., the compressive forces 482 can be applied to the ring 480) by a single hand of the wearer, such as by pinching the ring 480 with the thumb and forefinger of one hand of the wearer.

Figure 12A:
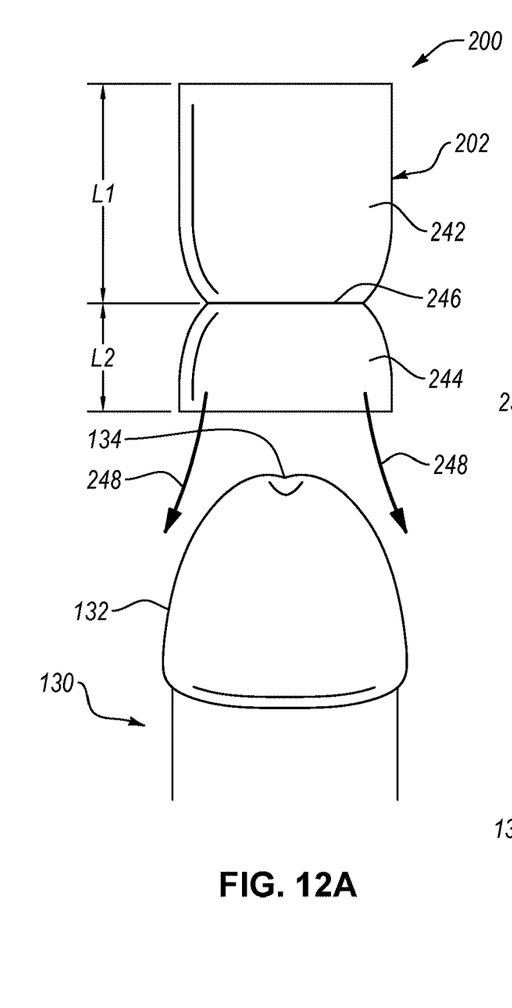
FIG. 12A is a schematic, top plan view of another sleeve for reducing involuntary urine leakage, according to one or more examples of the present disclosure.
Figure 12B:
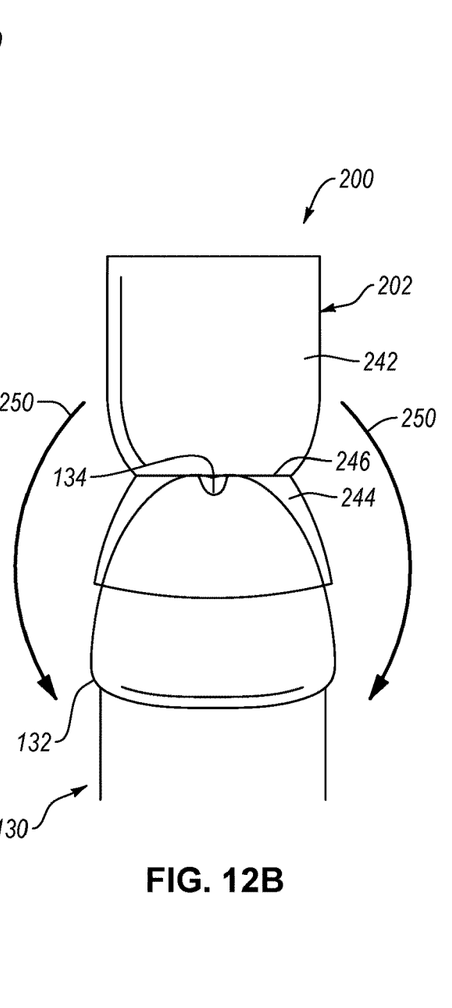
FIG. 12B is a schematic, top plan view of the sleeve of FIG. 12A partially retaining a penis, according to one or more examples of the present disclosure.
Figure 12C:
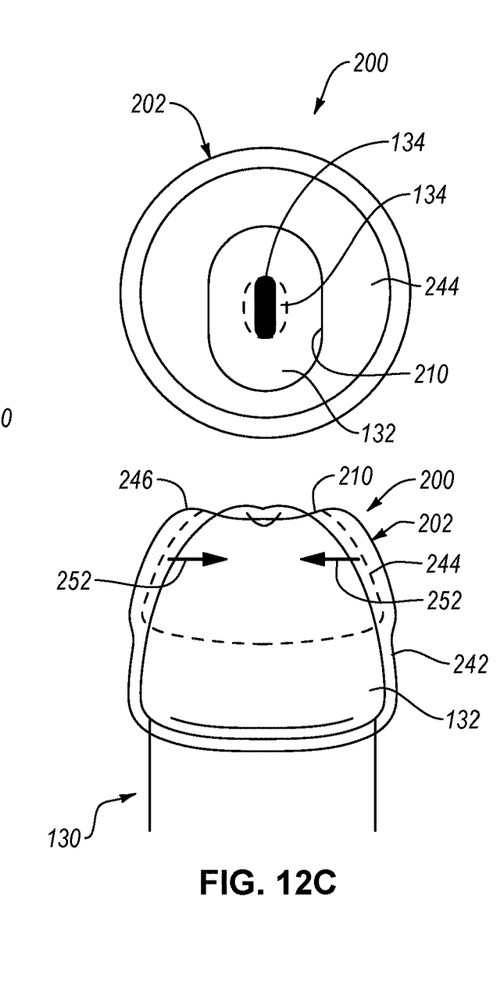
FIG. 12C is a schematic, top plan view of the sleeve of FIG. 12A fully retaining a penis, according to one or more examples of the present disclosure.

According to other examples, as shown in FIGS. 12A-12C, disclosed herein is a sleeve 200 for reducing involuntary urine leakage associated with male urinary incontinence. Like the sleeve 100, the sleeve 200 functions to apply inwardly-directed forces 252 on the glans penis 132 to close the urethral meatus 134. However, instead of opposing pads, such as the pads 118, which apply the inwardly-directed forces 142 along a single plane, the sleeve 200 applies the inwardly-directed forces 252 along multiple planes. More specifically, the sleeve 200 applies a substantially uniform radially-inwardly directed pressure around the entirety of the glans penis 132, which acts to close the urethral meatus 134.

The sleeve 200 includes a body 202 made of an elastic material. The body 202 includes a flap portion 242 and a receptacle portion 244. The flap portion 242 and the receptacle portion 244 are coupled together at a fold line 246 that divides the body 202 into the flap portion 242 and the receptacle portion 244. A central channel extends along an entirety of the body 202. The central channel, at the fold line 246, has a non-circular shape (e.g., ovular, elongated, elliptical, racetrack, etc.) in some examples, such that when the flap portion 242 is folded over the receptacle portion 244, as described below, the non-circular shape of the central channel at the fold line 246 becomes the non-circular shape of a distal opening 210 of the sleeve 200.

As shown in FIG. 12A, in some examples, a length L1 of the flap portion 242 is greater than a length L2 of the receptacle portion 244. The receptacle portion 244 tapers in a direction toward the fold line 246. Similarly, the flap portion 242 tapers in a direction toward the fold line 246. Accordingly, the portion of the central channel within the receptacle portion 244 defines a receptacle for receiving a tip portion of the glans penis 132, as shown in FIG. 12B, after the sleeve 200 is moved toward the glans penis 132 in the insertion direction 248, as shown in FIG. 12A. With the glans penis 132 received in the receptacle portion 244 of the body 202, the flap portion 242 of the body 202 is flipped, folded, or rolled about the fold line 246 over the receptacle portion 244 in the folding direction 250. As shown in FIG. 12C, when folded over the receptacle portion 244, the flap portion 242 envelopes the receptacle portion 244 and covers the glans penis 132 except for a portion of the glans penis 132 that is open to the distal opening 210 in the body 102. Due to the elasticity of the flap portion 242, the flap portion 242 is stretched when folded about the fold line 246 over the receptacle portion 244. The resilient stretch in the flap portion 242 results in the application of the inwardly-directed forces 252 to the receptacle portion 244, which are in turn applied to the glans penis 132 to close the urethra meatus 134, which is show open in dashed lines in FIG. 12C.

Although not shown, in some examples, the sleeve 200 includes pads, similar to the pads 118 of the sleeve 100, that extend from opposing sides of an internal surface of the receptacle portion 244. The pads 118 can be positioned on opposite sides of the sagittal plane 136 of the user when worn and thus can help to promote inwardly directed forces on the glans penis 132 perpendicular to the sagittal plane 136 in a manner similar to that associated with the pads 118 of the sleeve 100.

The wearer can remove the sleeve 200 by unfolding the flap portion 242 from around the receptacle portion 244, which releases the inwardly-directed forces 252 (e.g., to effectively unclamp the receptacle portion 244 from the glans penis 132). The wearer can then simply remove the sleeve 200 from the glans penis 132 in a direction opposite the insertion direction 248. Furthermore, to allow for voluntary urination, the wearer can keep the receptacle portion 244 on the glans penis 132 after the flap portion 242 is unfolded to open the urethral meatus 134. After voluntary urination, the flap portion 242 can be re-folded around the receptacle portion 244 to again close the urethral meatus 134. Alternatively, in certain examples, the sleeve 200 can includes tabs, similar to the tabs 112 of the sleeve 100, to help facilitate temporary opening of the urethral meatus 134 for voluntary urination.

According to yet other examples, as shown in FIGS. 13A-14D, disclosed herein is a sleeve 300 for reducing involuntary urine leakage associated with male urinary incontinence. Like the sleeve 200, the sleeve 300 functions to apply inwardly-directed forces 352 on the glans penis 132 to close the urethral meatus 134. However, instead of applying a substantially uniform radially-inwardly directed pressure around the entirety of the glans penis 132, the sleeve 300 applies the inwardly-directed forces 352 along a single plane, similar to the pads 118.

Figures 13A, 13B:
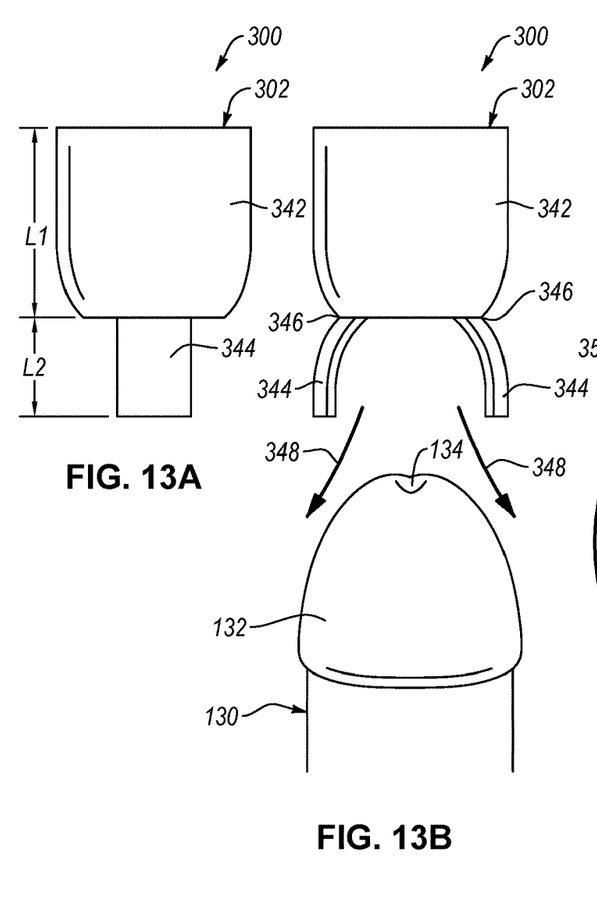
FIG. 13A is a schematic, side elevation view of another sleeve for reducing involuntary urine leakage, according to one or more examples of the present disclosure.
FIG. 13B is a schematic, top plan view of the sleeve of FIG. 13A, according to one or more examples of the present disclosure.

The sleeve 300 includes a body 302 made of an elastic material. The body 302 includes a flap portion 342 and a pair of receptacle tabs 344. The flap portion 342 and the receptacle tabs 344 are coupled together at fold lines 346 that divide the body 302 into the flap portion 342 and the receptacle tabs 344. A central channel extends along the flap portion 342 of the body 302. As shown in FIG. 13A, in some examples, a length L1 of the flap portion 342 is greater than a length L2 of the receptacle tabs 344. The receptacle tabs 344 converge in a direction toward the fold line 346. Similarly, the flap portion 342 tapers in a direction toward the fold line 346.

Figure 13C:
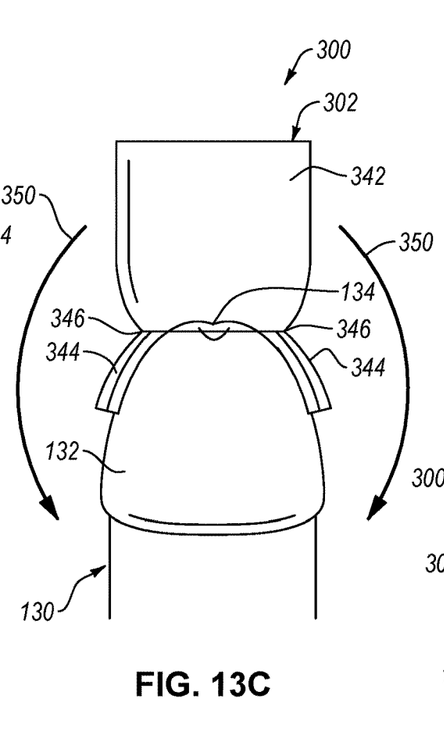
FIG. 13C is a schematic, top plan view of the sleeve of FIG. 13A partially retaining a penis, according to one or more examples of the present disclosure.
Figure 13D:
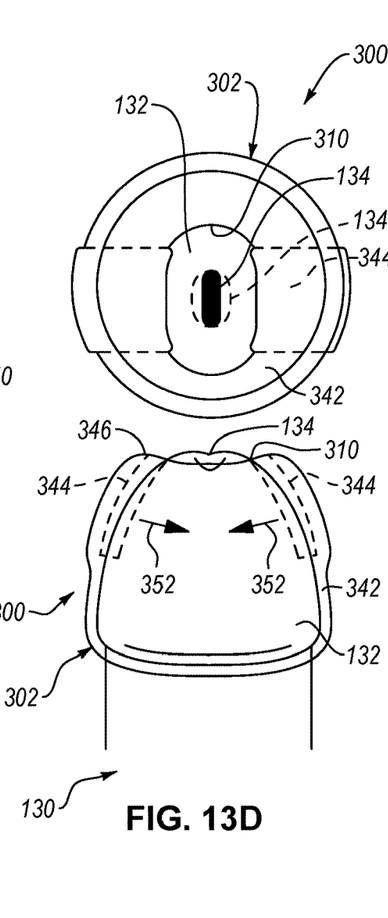
FIG. 13D is a schematic, top plan view of the sleeve of FIG. 13A fully retaining a penis, according to one or more examples of the present disclosure.

The space between the receptacle tabs 344 defines a receptacle for receiving a tip portion of the glans penis 132, as shown in FIG. 13C, after the sleeve 300 is moved toward the glans penis 132 in the insertion direction 348, as shown in FIG. 13B. With the glans penis 132 received between the receptacle tabs 344, the flap portion 342 of the body 302 is flipped, folded, or rolled about the fold line 346 over the receptacle tabs 344 in the folding direction 350. As shown in FIG. 13D, when folded over the receptacle tabs 344, the flap portion 342 envelopes the receptacle tabs 344 and covers the glans penis 132. Due to the elasticity of the flap portion 342, the flap portion 342 is stretched when folded about the fold line 346 over the receptacle tabs 344. The resilient stretch in the flap portion 342 results in the application of the inwardly-directed forces 352 to the receptacle tabs 344, which are in turn applied to the glans penis 132 to close the urethra meatus 134, which is show open in dashed lines in FIG. 13D.

The wearer can remove the sleeve 300 by unfolding the flap portion 342 from around the receptacle tabs 344, which releases the inwardly-directed forces 352 (e.g., to effectively unclamp the receptacle tabs 344 from the glans penis 132). The wearer can then simply remove the sleeve 300 from the glans penis 132 in a direction opposite the insertion direction 348. Furthermore, to allow for voluntary urination, the wearer can keep the receptacle tabs 344 on the glans penis 132 after the flap portion 342 is unfolded to open the urethral meatus 134. After voluntary urination, the flap portion 342 can be re-folded around the receptacle tabs 344 to again close the urethral meatus 134. Alternatively, in certain examples, the sleeve 300 can includes tabs, similar to the tabs 112 of the sleeve 100, to help facilitate temporary opening of the urethral meatus 134 for voluntary urination.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two." Moreover, unless otherwise noted, as defined herein a plurality of particular features does not necessarily mean every particular feature of an entire set or class of the particular features.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The present subject matter may be embodied in other specific forms without departing from its spirit or essential characteristics. The described examples are to be considered in all respects only as illustrative and not restrictive. All changes which come within the meaning and range of equivalency of the claims are to be embraced within their scope. Examples of the scope of the present subject matter can be found in the following claims.

What is claimed is:

1. A sleeve for reducing involuntary leakage of a flowable material from a urethral meatus of a penis, the sleeve comprising:
  a body, configured to temporarily receivably retain a glans penis of a penis, wherein the body comprises:
    a cylindrical section;
    a conical section; and
    a receptacle defined by the cylindrical section and the conical section;
  wherein:
    when the glans penis is temporarily receivably retained by the body, the body applies an inwardly-directed pressure to the glans penis to close a urethral meatus of the glans penis;
    the body is configured to temporarily receivably retain the glans penis within the receptacle;
    the receptacle comprises a proximal opening defined by the cylindrical section and a distal opening defined by the conical section; and
    the proximal opening is larger than the distal opening.

2. The sleeve according to claim 1, wherein:
  the proximal opening has a circular shape; and
  the distal opening has a non-circular shape.

3. The sleeve according to claim 2, wherein the non-circular shape of the distal opening is one of an elliptical shape, an elongated shape, an ovular shape, or a racetrack shape.

4. The sleeve according to claim 1, wherein the body further comprises perforations located along the body between the proximal opening and the distal opening.

5. The sleeve according to claim 1, further comprising pads, wherein:
each one of the pads is coupled to an interior surface of the conical section of the body on opposite sides of the distal opening; and
the pads define a converging portion of the receptacle.

6. The sleeve according to claim 5, wherein:
each one of the pads comprises an engagement surface, configured to engage the glans penis; and
the engagement surface of each one of the pads is at least one of convex or concave.

7. The sleeve according to claim 6, wherein each one of the pads defines a corresponding one of two opposing linear sides of the distal opening of the receptacle.

8. The sleeve according to claim 5, wherein
the receptacle has a width, extending from a left side of the body to a right side of the body, and a length, extending from a back side of the body to a front side of the body;
the width of the receptacle, along the conical section of the body, is defined by the pads; and
a rate of convergence of the width of the receptacle, along the conical section of the body, is higher than a rate of convergence of the length of the receptacle, along the conical section of the body.

9. The sleeve according to claim 8, further comprising tabs each coupled to and extending laterally away from an exterior surface of the conical section of the body at a corresponding one of the left side and the right side of the body.

10. The sleeve according to claim 9, wherein each one of the tabs comprises an exterior surface and a rib that protrudes from the exterior surface.

11. The sleeve according to claim 9, wherein the tabs are pullable away from each other to increase the width of the receptacle at the distal opening.

12. The sleeve according to claim 8, wherein the width of the receptacle at the distal opening is less than the length of the receptacle at the distal opening.

13. The sleeve according to claim 1, further comprising a ring coupled to the conical section of the body, wherein:
the ring defines the distal opening;
the body is made of a first resiliently flexible material;
the ring is made of a second resiliently flexible material; and
a stiffness of the first resiliently flexible material is less than a stiffness of the second resiliently flexible material.

14. The sleeve according to claim 1, wherein the body is made of an elastic material.

15. The sleeve according to claim 1, wherein:
the body comprises a flap portion and a receptacle portion;
the flap portion and the receptacle portion are coupled together at a fold line that divides the body into the flap portion and the receptacle portion;
the flap portion and the receptacle portion taper to the fold line;
a central channel extends along an entirety of the body;
a portion of the central channel defined by the receptacle portion is shaped to receive a tip portion of the glans penis; and
a length of the flap portion is greater than a length of the receptacle portion such that when the body is folded at the fold line, the flap portion overlaps an entirety of the receptacle portion.

16. The sleeve according to claim 15, wherein a shape of the central channel at the flap portion is non-circular.

17. The sleeve according to claim 1, wherein:
the body comprises a flap portion and a pair of receptacle tabs, the receptacle tabs of the pair of receptacle tabs are opposite and spaced apart from each other;
the flap portion and the pair of receptacle tabs are coupled together at a fold line that divides the body into the flap portion and the pair of receptacle tabs;
the flap portion and the pair of receptacle tabs taper to the fold line;
a central channel extends along the flap portion of the body;
a space between the receptacle tabs is shaped to receive a tip portion of the glans penis; and
a length of the flap portion is greater than a length of each receptacle tab of the pair of receptacle tabs such that when the body is folded at the fold line, the flap portion overlaps an entirety of the pair of receptacle tabs.

18. A sleeve for reducing involuntary leakage of a flowable material from a urethral meatus of a penis, the sleeve comprising:
a body, comprising a receptacle configured to temporarily receivably retain a glans penis of a penis, wherein the receptacle comprises a proximal opening and a distal opening; and
pads coupled to an interior surface of the receptacle of the body on opposite sides of the distal opening;
wherein when the glans penis is temporarily receivably retained by the receptacle of the body, the pads apply an inwardly-directed pressure to the glans penis to close a urethral meatus of the glans penis.

19. The sleeve according to claim 18, wherein the pads define a converging portion of the receptacle.

20. The sleeve according to claim 19, wherein the proximal opening is larger than the distal opening.

* * * * *